United States Patent [19]
Giacopuzzi

[11] Patent Number: 5,657,780
[45] Date of Patent: Aug. 19, 1997

[54] DENTAL FLOSS HOLDER WITH WEDGE ACTUATED BRAKE ASSEMBLY

[76] Inventor: Guy G. Giacopuzzi, Lake Arrowhead Medical Center Suite 208 Box 68, Cedar Glen, Calif. 92321

[21] Appl. No.: 567,693

[22] Filed: Dec. 5, 1995

[51] Int. Cl.$^6$ .................................................. A61C 15/00
[52] U.S. Cl. .................................. 132/325; 132/326
[58] Field of Search .............................. 132/323, 324, 132/325, 326, 327

[56] References Cited

U.S. PATENT DOCUMENTS

| | | |
|---|---|---|
| D. 251,074 | 2/1979 | Schiff. |
| D. 251,075 | 2/1979 | Schiff. |
| 1,110,680 | 9/1914 | Gamble. |
| 1,627,525 | 5/1927 | Munro. |
| 1,916,653 | 7/1933 | Bodde. |
| 2,187,442 | 1/1940 | Beach. |
| 2,217,917 | 10/1940 | Munro. |
| 3,311,116 | 3/1967 | Foster. |
| 3,792,706 | 2/1974 | Keese. |
| 3,906,963 | 9/1975 | Jenkins et al.. |
| 4,151,851 | 5/1979 | Bragg. |
| 4,192,330 | 3/1980 | Johnson. |
| 4,214,598 | 7/1980 | Lee. |
| 5,105,840 | 4/1992 | Giacopuzzi ............... 132/325 |
| 5,197,498 | 3/1993 | Stewart ................... 132/325 |
| 5,269,331 | 12/1993 | Tanriverdi ............... 132/325 |
| 5,287,865 | 2/1994 | Fulton .................... 132/325 |
| 5,301,698 | 4/1994 | Ballard ................... 132/325 |

*Primary Examiner*—Gene Mancene
*Assistant Examiner*—Ralph A. Lewis
*Attorney, Agent, or Firm*—Law Offices of Gregory L. Roth

[57] ABSTRACT

A strong, light weight, highly maneuverable dental floss holder has two centrally pivoted support members with holding sections extending on one side of the pivot and a pair of handle sections extending on the other side. Storage for new and used dental floss is provided by supply and take up reels located between the pair of handle sections. The handle sections terminate with a wedge actuated break assembly that restricts undesirable motion of the supply and take up reels. With single hand operation tension of the floss between the tips of the holding sections can be readily controlled and the dental floss can be selectively advanced.

19 Claims, 2 Drawing Sheets

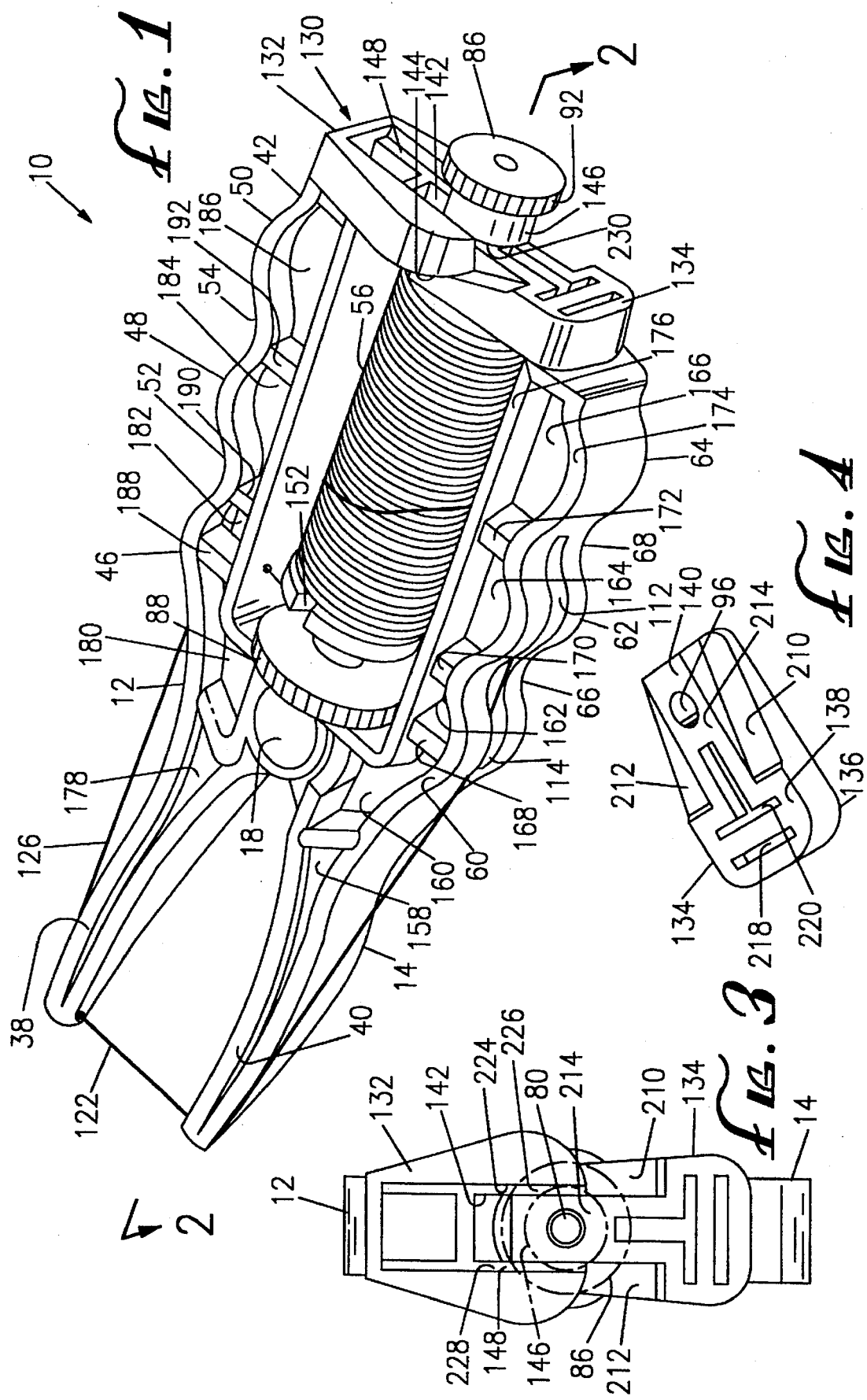

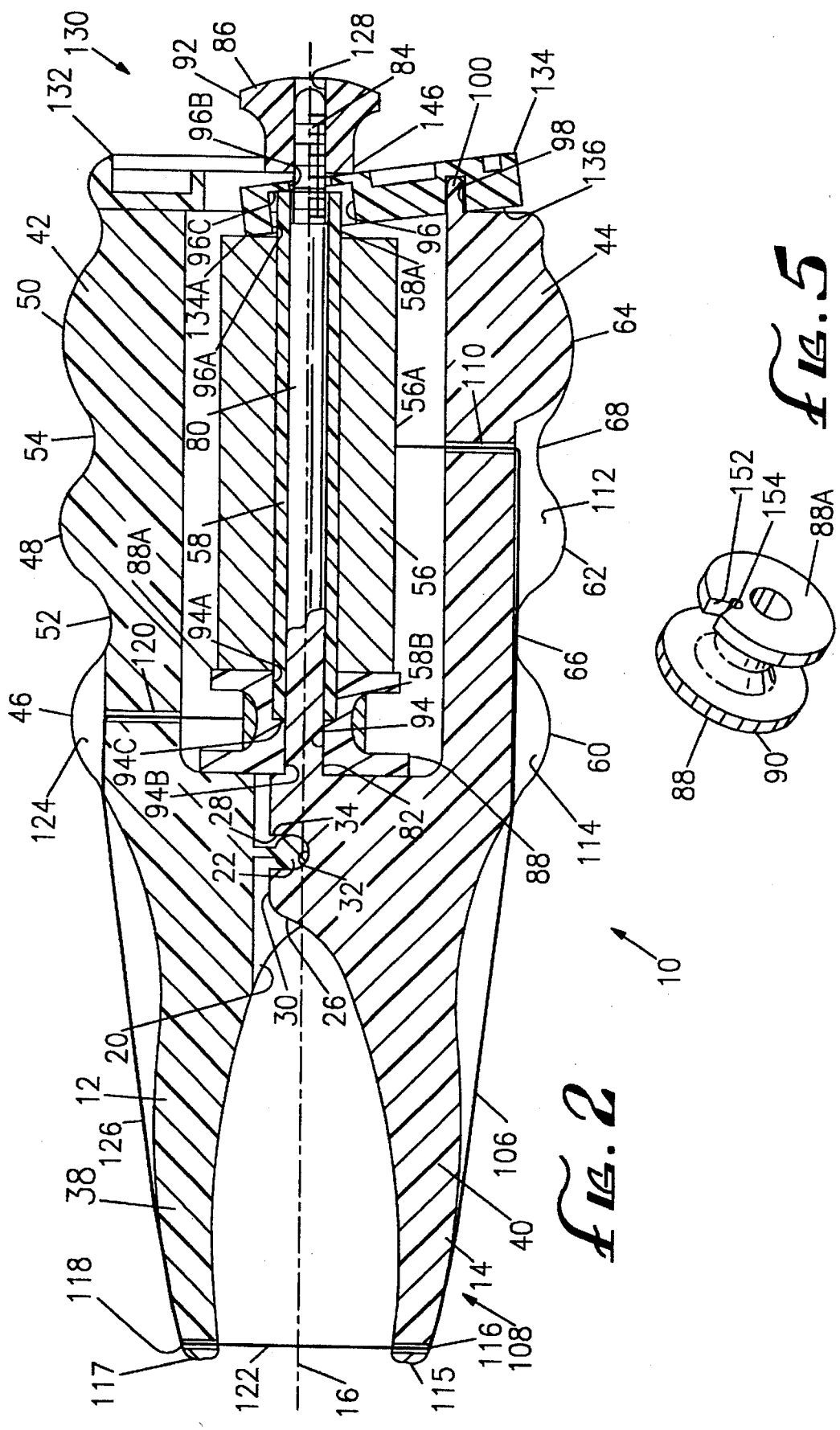

DENTAL FLOSS HOLDER WITH WEDGE ACTUATED BRAKE ASSEMBLY

BACKGROUND OF THE INVENTION

The benefits of using dental floss for removal of plaque from teeth have been known for many years. Daily flossing is recommended by almost all dentists. Nevertheless, because of the difficulty and inconvenience involved in manipulating the floss and the time delay of several minutes that is involved, very few people actually use dental floss on a daily basis.

Because of the difficulty of access to the back teeth, proper flossing is not an easy accomplishment. Initially the floss must be positioned in the space between two adjacent teeth. This positioning requires passing the floss through a narrow contact region between the teeth which is typically 0.25 to 1.25 millimeters deep. As the floss passes through this contact region it encounters considerable resistance and must be drawn tight in order to provide sufficient force for passage through the contact region.

The space beneath contact region is filled with a wedge shaped piece of soft tissue known as the gingival papilla. Care must be taken to assure that the floss does not suddenly "snap" through the contact region between the teeth while under tension and damage the gingival papilla between the teeth. Frequently bleeding of the gingival tissue is induced by traumatic contact with the floss as the floss snaps through the contact region.

To prevent this gingival damage the force on the dental floss must be reduced substantially just as the floss passes beneath the contact. This requires considerable dexterity and control. Once the floss is positioned beneath the contact, it should be allowed to partially wrap around the tooth to about 100 degrees of arc. It can then be passed between the papilla and one of the teeth as flossing proceeds.

Next the floss is moved to the adjacent tooth, still within the gap. The floss is then wrapped about the adjacent tooth and the flossing process is repeated before the floss is withdrawn from the interproximal gap. At this point the tension on the floss must again be increased as the floss is forced back through the contact region and out of the interproximal gap.

Studies have shown that the dental floss can transport bacteria from one quadrant of the mouth to another. In addition, waxed dental floss is frequently used to facilitate the flossing operation. The wax neither helps nor hinders the actual flossing operation, but does provide lubrication to make it easier to pass the floss through the contact region. However, the wax tends to come off the floss after two or three teeth have been flossed. It is therefore desirable to be able to store a supply of floss in the floss holder and advance a new length of floss to an active section at frequent intervals. At a minimum, the floss should be advanced for each different quadrant of the mouth.

Because floss is most conveniently available in standard 200 yard and 200 meter spools, it is desirable that the floss holder be able to accommodate such a spool. It is further desirable that the floss holder provide storage for used floss. This enables the user to delay final disposal of the used floss to a time that is most convenient to the user.

One of the problems associated with flossing is the time required each day for proper flossing. However, this time requirement would be no problem if the flossing could be done while a person is engaged in some other confining activity, such as driving an automobile. This would of course require a holder that could be controlled with one hand to provide proper manipulation and tensioning as well as advancement of the floss from a supply spool to a take up mechanism.

Several different floss holder devices have been developed to assist in the flossing operation. My present invention is an improvement of my earlier invention of Dental Floss Holder, U.S. Pat. No. 5,105,840. That patent teaches a convenient, precisely controllable dental floss holder which can be easily held and properly manipulated with one hand. The control of a dental floss supply reel, which was located between two handles of the dental floss holder, was achieved by squeezing both handles toward each other whereby a stop extended from one of the handles to press against dental floss wound on the supply reel, thus preventing rotation of the supply reel. A nut was provided to secure the dental floss supply reel. Tightening the nut produced a frictional braking action to help prevent undesirable rotation of the supply reel.

None of the other earlier inventions were able to satisfy all of the requirements of an ideal floss holder. For example, U.S. Pat. No. 1,110,680 to Gamble teaches a "scissor" type of floss holder. The holder provides looped type handles that are difficult to hold and do not facilitate proper control of floss position and tension. Two hands are required to advance the floss and there is no storage for used floss. The floss supply mechanism cannot accommodate a standard 200 yard supply spool.

U.S. Pat. No. 4,192,330 to Johnson teaches a principle embodiment that uses a fixed cartridge. Once the cartridge is inserted, the floss is locked in tension without convenient adjustment. The cartridge must be replaced to obtain a new length of floss. Several such replacements would not be practical during a single flossing operation. In an alternative arrangement, a fixed length loop of floss is attached to the holder and then subjected to constant tension. The tension cannot be adjusted as appropriate for a proper flossing operation.

U.S. Pat. No. 3,792,706 to Keese discloses a holder in which a length of floss is secured to the ends thereof. In one embodiment the ends may be manipulated in response to finger pressure in order to change the tension. However, the control leverage arm is too short to provide adequate control over tension. In an alternative embodiment the holder arms can flex, but this cannot provide adequate control over floss tension.

U.S. Pat. No. 3,906,963 to Jenkins et al. teaches an arrangement in which a thumb screw can control the spacing between holder arms. Such a screw is too slow and inconvenient to represent a practical tooth by tooth adjustment. The floss is maintained under constant tension by a spring. No quick, convenient manual control of floss tension is provided.

U.S. Pat. No. 4,151,851 to Bragg teaches a holder having supply and take up reels on opposite sides thereof. The holder does not allow immediate manual control over floss tension and a long narrow handle makes precise positioning and control of the holder difficult.

U.S. Pat. No. 4,214,598 to Lee discloses supply and take up reels on a nonadjustable holder.

U.S. Pat. No. Des. 251,075 to Schiff and U.S. Pat. No. Des. 251,074 to Schiff show floss holders which use a fixed length of floss that cannot be advanced. The holder would appear to provide limited control over floss tension.

SUMMARY OF THE INVENTION

A convenient, precisely controllable dental floss holder in accordance with the invention can be easily held and properly manipulated with one hand. The holder includes a pair of generally straight parallel, spaced support members that are pivotably joined in a central region thereof in noncrossing relationship. A pair of support sections extend from the central region in a forward direction to terminate in a pair of spaced tips. A pair of hand sized handle sections that are approximately equal in length to the support sections extend from the central region in a rearward direction opposite the pair of support members. Supply and take up mechanisms for dental floss are disposed between the handle sections. A shaft extends rearwardly from the central region of one of the support members and supply and take up reels are mounted for rotation on the shaft. The handle end of the holder terminates with a wedge actuated break assembly which includes a control knob and two overlapping endplates, each secured to a different handle section. One of the endplates pivots relative to the handle section and is removable. The endplates provide between them a wedge shaped surface that produces a cammed braking force in response to handle closure forces to enable one handed control over the force required for rotation of the dental floss supply and take up reels.

A floss path is provided in the support members from the supply reel, past the spaced apart tips and then to the take up reel. The handle sections are shaped to conform to the shape of a user's hand. The spacing between the tips, and hence floss tension, is readily controlled by opening and closing the handle sections. Manual compression or closure of the handle sections by squeezing tends to separate the tips to increase the tension on the floss while increasing braking forces on the supply and take up reels. Relaxation of the handle force reduces the tension and allows the natural force of floss against a tooth to close the tips while opening the handle sections. Slack is thus provided to enable the floss to wrap part way around a tooth as it forms a "C" shape. The thumb and index finger can exert force on the take up mechanism that can be used concurrently with the breaking force to help control floss tension.

With single handed operation a user can tension the floss as it passes through the contact region between two teeth. As soon as the floss passes through the contact region and into an interproximal gap between two teeth, the hand may be relaxed somewhat to reduce floss tension and avoid damage to the gingival papilla. While the floss remains in the interproximal gap, the floss can be sequentially wrapped part way around each tooth adjacent to the gap as proper flossing action is completed. The floss can then be tightened by merely squeezing the hand as the floss passes back past the contact region for removal from the interproximal gap. Still with a single hand, the thumb and index finger may push against a take up spool to advance the floss and position a fresh length of floss between the tips. Further control of dental floss tension is achieved by turning a control knob to tighten the removable endplate against the supply reel and apply a minimum breaking force that resists rotation of the supply and take up reds.

BRIEF DESCRIPTION OF THE DRAWINGS

A better understanding of the invention may be had from a consideration of the following Detailed Description, taken in conjunction with the accompanying drawings in which:

FIG. 1 is a perspective view of a dental floss holder in accordance with the invention;

FIG. 2 is a sectional view of the dental floss holder shown in FIG. 1;

FIG. 3 is an end of the dental floss holder shown in FIG. 1, taken from the rear with the knob removed;

FIG. 4 is a perspective view of a removable endplate; and

FIG. 5 is a perspective view of a take up reel.

DETAILED DESCRIPTION OF THE INVENTION

Referring now to FIGS. 1 and 2 a single-handed, tension controllable dental floss holder with a handle controlled, wedge actuated break assembly 10 in accordance with the invention includes two elongated, substantially straight support members 12, 14 disposed in generally parallel opposed, spaced apart relationship on opposite sides of a longitudinally extending central axis 16. While held in the right hand, support member is intended to engage the thumb base or the palm of a user while support member 14 is intended to engage the fingers of a user such that the floss holder 10 is conveniently held with a single hand. To accommodate left-hand or right-hand use, support members 12, 14 are designed to be substantially symmetrical and therefore when held in the left hand, support member 12 is also intended to engage the fingers while support member 14 engages the base of the thumb or the palm of the left hand. A central pivot support 18 is located approximately midway along the length of elongated support member 12 and extends inwardly toward the other support member 14 and central axis 16. Pivot support 18 has a longitudinally extending slot or recess 20 formed therein. A small cylindrical pivot pin 22, which may be molded as an integral part of support member 12, extends transversely across the slot 20.

Elongated support member 14 has a protrusion in the form of a mating tongue 26 that extends inwardly past central axis 16 toward elongated support member 12 where it is matingly received within the slot 20. Tongue 26 is somewhat narrower than the remainder of support member 14 in order that it may be received within the slot 20. Tongue 26 further has a transversely extending recess 28 in the end 30 thereof that matingly receives the cylindrical pivot pin 22. Recess 28 has a cylindrical base 32 which is equal in diameter to pivot pin 22 and which matingly receives and retains the pivot pin 22. An outer portion 34 of recess 28 is slightly smaller than the diameter of pivot pin 22 such that upon assembly pivot pin 22 passes with a force fit through the outer portion 34 and snaps into place in mating relationship within the cylindrical base portion 32 to normally maintain the support members 12 and 14 in a pivotally connected relationship. The central axis of pivot pin 22 is spaced a short distance from central longitudinal axis 16 toward the support member 14, but lies substantially on longitudinal axis 16.

The support members 12, 14 extend in generally parallel, noncrossing relationship. The support members 12, 14 each have a holding section 38, 40 which extend on a forward side of the pivot pin 22 and a handle sections 42, 44 which extend rearwardly from the pivot pin 22 opposite the holding sections 38, 40 respectively. Holding sections 38, 40 are curved upward (out of the plane of the paper as shown in FIGS. 1 and 2) at an angle of about 8°–10° relative to central axis 16 and handle sections 42, 44 to facilitate placement of the floss between two teeth. The handle section 42 of support member 12 is shaped to comfortably mate in non-slip relationship with the palm of a user or the base of a user's thumb and has three outwardly extending ridges 46, 48, 50 separated by intermediate valley sections 52, 54. The handle section 44 of support member 14 has three outwardly extending ridges 60, 62, 64 separated by intermediate valleys 66, 68 to comfortably receive the fingers of a use'hand and to provide a secure, non-slip grip. The large, hand sized handle sections 42, 44 combine with the ridges and valleys thereon to enable the user to firmly hold the floss holder 10 in one hand in a firm and non-slip comfortable manner while the user asserts the necessary manipulations and forces to perform a dental flossing operation.

In the preferred embodiment, the dental floss holder is made of medical grade ABS plastic. To reduce the weight and material costs and facilitate molding, the top side 158 of handle section 44 of support member 14 includes cavities 160, 162, 164, 166 extending substantially along the longitudinal axis 16. Each cavity 160, 162, 164, 166 extends downwards 2/3 of the total height of the handle section 44. Ribs 168, 170, 172 extend transversely from the outer edge 174 to the inner edge 176 of handle section 44 to provide additional rigidity and strength. The bottom side (not shown) of handle section 44 of support member 14 includes cavities and ribs which mirror cavities 160, 162, 164, 166 and ribs 168, 170, 172. As mentioned previously, handle sections 42, 44 of support member 12,14, respectively, are substantially symmetrical and thus, the top side 178 of handle section 42 includes cavities 180, 182, 184, 186 and ribs 188, 190, 192 substantially identical to cavities 160, 162, 164, 166 and ribs 168, 170, 172. Similarly, the bottom side (not shown) of handle section 42 includes cavities and ribs which mirror cavities 180, 182, 184, 186 and ribs 188, 190, 192.

A shark or spindle 80 (see FIG. 2), which can be molded from plastic, has a fixed central end 82 secured to the inwardly projecting tongue 26 of support member 14 and extends rearward along central axis 16. Shaft 80 and support member 14 can be molded as one integral piece. At least the distal rearward end 84 of shall 80 is threaded so as to receive in threaded relationship a control knob 86. The knob 86 may also be made of medical grade ABS plastic and includes a threaded axially extending bore 128 which threadably engages shaft 80. Control knob 86 has a roughened or knurled flange 92 to facilitate non-slip engagement between the fingers of a user and the knob. The shaft 80 receives a rotatable take up reel 88 adjacent the central end 82 thereof and a rotatable supply reel of dental floss 56 outwardly of the take up reel 88. Supply reel 56 is available from commercial suppliers and contains a length of floss wound onto a hollow cylindrical hub 58 having ends 58A and 58B which extend beyond the floss winding on opposite ends thereof. It will be appreciated that the relative locations of the take up reel 88 and supply reel 56 could be reversed. However, in the preferred embodiment the take up reel 88 is located inwardly of supply reel 56 so as to enable the thumb of a user to engage the outer periphery of take up reel 88 and manipulate the rotational position thereof so as to continually control floss tension during a flossing operation and also to easily advance the dental floss by rotating the take up reel while flossing proceeds. The exterior of take up reel 88 has a roughened or knurled flange 90 to facilitate non-slip engagement between the thumb of a user and the take up reel 88. The control knob 86 may be selectively tightened to control the force required to rotate supply reel 56 and take up reel 88.

Take up reel 88 has an axially extending central bore 94 which receives shaft 80 therethrough. The rearward end of bore 94 has a larger diameter portion 94A which receives the extend end 58B of hub 58 in mating relationship. The forward end 94B of bore 94 has a smaller diameter than portion 94A. The diameter of portion 94B is large enough to receive shaft 80 therethrough but too small to receive end 58B of hub 58 therethrough. The end of hub 58 thus buts up against a transition 94C between smaller diameter portion 94B and larger diameter portion 94A. The axial length of larger diameter portion 94A of bore 94 is selected to be slightly shorter than the extended end 58B of hub 58. A small clearance is thus maintained between the rearward surface of take up reel 88 and a forward surface of the floss winding on hub 58.

The handle sections 42, 44 terminate with a wedge actuated, manually controlled break assembly 130 consisting of the control knob 86 and two overlapping endplates 132, 134 which define a wedge shaped surface between them. Endplate 134 pivots relative to handle section 44 and has its inner end placed forward of the endplate 132. The endplates 132, 134 provide a wedge actuated break arrangement that enables one handed control over the force required for rotation of the dental floss supply reel 56 and take up reel 88. Referring now to FIGS. 2–4, endplate 134 has a cylindrical aperture 96 adjacent an overlapping inward end which receives the distal end of shaft 80 therethrough. Aperture 96 has a large diameter forward portion 96A which receives hub end 58A and a smaller diameter rearward portion which is large enough to receive shaft 80 therethrough, but too small to receive hub end 58A. Aperture 96 passes through a nonwedge shaped portion of endplate 134 near the inner end thereof.

The axial length of the larger diameter portion 96A of bore 96 is slightly smaller than the length of the extended end 58A of hub 58. The rearward end of hub 58 thus buts up against a transition 96C between larger diameter portion 96A and smaller diameter portion 96B of bore 96 to maintain a small clearance between the floss winding on hub 58 and the forward surface 136 of endplate 134. Endplate 134 has a rectangular aperture or recess 98 at an outer end opposite aperture 96. The distal rearward end of handle section 44 terminates in a small rectangular cross sectioned tab 100 which extends into and matingly engages the rectangular aperture or recess 98. End plate 134 is substantially rectangular and has a forward flat forward surface 136 that is substantially flat.

Endplate 134 has a surface 138 opposite surface 136 that is also generally flat except for two wedge shaped, planar cuts 210, 212 on opposite sides thereof. A central, nontapered, nonwedge shaped rectangular section 214 extends like a tongue between the two wedge shaped sections 210, 212 and receives the aperture 96. Two wedge shaped, tapered surfaces 218, 220 are formed in the rearward surface 138 of endplate 134 on opposite sides of section 214. Section 214 is matingly received by a slot 142 of backplate 132. The rearward surface of backplate 132 further includes an enlarged slot 224 which extends on either side of slot 142. The depth of slot 224 is selected to make the thickness of backplate 132 beneath slot 224 less than or equal to the thickness of rectangular portion 214 of endplate 134 when endplate 132 engages the thinner part of wedges 212, 214. A shoulder 148 thus extends peripherally within slot 142 to engage the periphery of a disk shaped forward surface 146 of the control knob 86. Endplate 132 is permanently attached to the distal end of handle section 42 and can be molded as one integral part. The forward side 144 of endplate 132 is tapered to matingly engage the tapered outward side 138 of endplate 134.

Endplate 134 is readily removed by removing control knob 86 and pulling endplate 134 from shaft 80 and tab 100. The supply reel of dental floss 56 is thus fully released and may be selectively removed and replaced with a fresh reel of dental floss. Endplate 134 is then replaced with aperture 96 receiving the distal end of shaft 80 and cavity 98 receiving the distal end of tab 100. Control knob 86 may then be tightened on the distal end 84 of shaft 80 to secure endplate 134 in place and force endplate 134 and the supply reel hub 58 forward toward the central or pivot region of holder 10. By controlling the tightness of control knob 86 a user can selectively control the minimum forces required to rotate take up reel 88 and supply reel 56 relative to the holder 10. Endplate 134 serves to support the distal end 84 of shaft 80 by receiving shaft 80 through bore 96 and in particular prevents the shaft from accidentally breaking or bending toward tab 100 when handle sections 42, 44 are squeezed together by a user to engage the wedge actuated break assembly 130.

As the handle sections 42, 44 are closed by squeezing them together, the nonwedge shaped rectangular portion 214 moves within slotted recess 142 and the tapered ends of endplate 132 bear against the wedge shaped surfaces 210, 212 of endplate 134. The wedge action between endplate 132 and endplate 134 creates a forward directed force on endplate 134 which compress hub 58 of supply reel 56 between transition 96C of the bore 96 of endplate 132 and transition 94C of bore 94 through take up reel 88. The depth of transition 96C is selected to match the distance by which the rearward end of floss hub 58 extends beyond the actual floss winding 56A. Consequently, the forward outer edge 134A of endplate 134 frictionally engages winding 56A as transition 96C frictionally engages the rearward end of hub 58 as braking force is applied.

Similarly the depth of transition 94C is selected to match the amount by which the forward end of hub 58 extends beyond the actual floss winding 56A. Consequently, a rearward surface 88A of take up reel 88 frictionally engages a forward surface of the actual floss winding 56A while the forward end of hub 88 frictionally engages transition 94C when breaking force is applied. This frictional engagement creates a frictional braking action that increases the difficulty of rotating take up reel 88, hub 58 and supply reel 56 in proportion to the squeezing force asserted by the handle sections 42, 44. The application of braking force to both the actual floss winding 56A and the hub 88 assures that the floss winding 56A is restrained even if winding 56A is loosely wound on hub 88 as is able to rotate relative to hub 88.

The enlarged slot 224 surrounding recess 142 enables control knob 86 to bear against endplate nontapered section 214 to maintain a selected, minimum breaking force against hub 58. At the same time, the enlarged slot 224 initially allows the end of endplate 134 to slide beneath forward facing, disk shaped surface 230 of control knob 86 as the handle sections 42, 44 are squeezed together. However, as the handle sections 42, 44 are squeezed hard enough to produce a wedge induced breaking action, rearward facing surfaces 226, 228 of slot 224 are forced into engagement with the outer periphery of the forward facing surface 230 of control knob 86. The rearward force which counteracts the forward directed breaking force on hub 58 is thus absorbed by control knob 86 and shaft 80 and is not passed to the joint between endplate 132 and handle section 42. The reliability of holder 10 is thus substantially improved.

A dental floss path 108 is defined from the supply reel 56 past the tips 115, 117 of the support members 42, 44 and back to the take up reel 88. A hole 110 is drilled through the handle section 44 of support member 14 in the vicinity of a rearward valley 68 which is positioned approximately midway along the axial length of supply reel 56. Longitudinally extending slots 112, 114 are formed in ridges 62, 60 respectively and a hole 116 is formed in the tip or distal end 115 of holding section 40 of support member 14. The path 108 continues across to a hole 118 in the tip or distal end 117 of holding section 38 of support member 12 and then through a hole 120 in the handle section 48 of support member 12 near the center pivot of support member 12 and in juxtaposition with the take up reel 88. The floss path 108 thus extends from supply reel 56 through the hole 110, through slots 112, 114 in the handle section 42 of support member 14, and then through hole 116 in the tip 115 of support member 14. From the tip 115 of support member 14 the path extends across to the tip 117 of support member 12 where it passes through a hole 118 and then extends back toward the handle section 44 to pass through a slot 124 in a protrusion 60 of the handle section 44. The floss then extends through a hole 120 to be wound upon the take up reel 88.

The holding sections 38, 40 extend at an angle of approximately 9° relative to the handle sections 42, 44 to facilitate placement of the floss 122 adjacent a contact region between two teeth. That is, as shown in FIGS. 1 and 2, if the back side of handle sections 42, 44 are lying on a planar surface, the holding sections 38, 40 extend above the planar surface at an angle of approximately 9°, beginning at the pivot support 18.

Referring now to FIG. 5, in the preferred embodiment, a transverse V-shaped slot 152 is provided for the floss 106 to be secured to take up reel 88. Adjacent to the narrow, radially inward end of the slot 152 is a knot hole 154. The floss 106 can be secured to the take up reel 88 by tieing a knot such as a single overhand knot on an end of a length of floss 106, and inserting the floss through slot 152 into hole 154 and then pulling the floss 106 through hole 154 until the knot prevents passage of floss 106 through the hole 154. Alternatively, the floss can be secured to reel 88 by merely winding two or three turns of floss thereon until a non-slip engagement is secured between the floss and the reel 88.

During use, the user selectively closes and squeezes the handle sections 42, 44 to spread the tips and compress the hub 58 and floss 56A of supply reel 56 between the transition 96C and edge 134A of endplate 134 of the wedge actuated break assembly 130 and the transition 94C and surface 88A of the take up reel 88. As the floss holder 10 is positioned to pass a length of floss 122 through an interproximal contact, the user's thumb is asserted against take up reel 88 and the handle sections 42, 44 are squeezed to tighten the floss 106 along the floss path 108. An active length of floss 122 between the holder tips is then positioned in the mouth opposite a tooth contact and, with the floss 106 held in tension, is forced through the interproximal contact. As the active length 122 passes through the interproximal contact, the grip may be relaxed to allow the tips to move closer together and provide slack at the active length of floss 122. At the same time the thumb grip on reel 88 may be relaxed to further increase the length of active floss in section 122 to permit the floss to wrap part way around the tooth inside of the gingival papilla to form a C-shaped partial loop about the tooth. Flossing may then proceed. Flossing is then repeated for the adjacent tooth of the contact before the grip is tighten and the thumb hold on take up reel 88 is tighten to increase the tension on the active length of floss 122 and remove the floss from the interproximal contact. If desired, a fresh length of floss may now be advanced to the active length of floss 122 between the holder tips before flossing the next interproximal contact. This floss advancement may be accomplished while continuing single hand manipulation of the holder 10 by merely relaxing the grip so as to release endplate 132 from supply reel 56 while rotating the take up reel 88 with the thumb.

Studies have shown that it is desirable to advance the active length of floss 122 at least for each separate quadrant of the mouth so as to preclude a contaminated section of floss 106 from acting as a carrier of infection from one quadrant of the mouth to another. If this is not done the floss may pick up bacteria at one interproximal contact and spread the bacteria to another noninfected contact. In addition, most people prefer to use a waxed type of dental floss. The wax does not aid or improve the flossing activity itself, but does act as a lubricant to enable the active length of floss 122 to more readily negotiate the contact region between adjacent teeth. The wax tends to wear off after two or three contacts have been negotiated and it is therefore desirable to frequently advance the floss 106 so that a freshly waxed length of floss lies between the two tips at all times. The holder 10 not only provides a convenient and comfortable holder for proper flossing operations, but also enables one handed manipulation of the holder 10 to easily and quickly advance a length of floss so that a fresh length of floss is readily provided to the active length of floss 122.

The take up reel 88 has a much smaller capacity than the supply reel 56. However, the take up reel 88 has sufficient capacity for about 180 flossings. Any time it is desired to empty the take up reel, the floss is simply cut at a suitable location such as at a cut point 126 along the support section 38 of holder 12. The newly freed end of used floss is then pulled until all floss has been removed from the take up reel 88. If desired, the tension knob 86 can be loosened slightly to allow reel 88 to turn more freely and then retightened after the used floss has been removed. The cut end of floss 106 is then passed through the remainder of floss path 108 and wound upon take up reel 88 until properly secured thereto.

While there has been shown and described above a particular arrangement of a single handed floss holder with a wedge actuated, handle controlled brake assembly in accordance with the invention for the purpose of enabling a person of ordinary skill in the art to make and use the invention, it will be appreciated that the invention is not limited thereto. Accordingly, any modifications, variations or equivalent arrangements within the scope of the attached claims should be considered to be within the scope of the invention.

What is claimed is:

1. A dental floss holder comprising:
   a pair of centrally pivotally connected support members, each having opposed handle sections and opposed support sections, each opposed support section terminating at a tip;
   a supply reel of dental floss disposed between the handle sections, the dental floss holder defining a floss path that extends from the supply reel to the tip of one of the pair of support members and between tips of the pair of support members; and
   a wedge actuated brake assembly having a wedge surface, the wedge actuated breaking assembly applying to the supply reel a braking force that resists supplying dental floss to the floss path in response to squeezing the two handle sections toward one another.

2. A dental floss holder according to claim 1 further comprising:
   a take up reel; and
   a shaft disposed along a longitudinal axis between the opposed handle sections, the shaft being secured to one of the handle sections and the shaft receiving and supporting the take up reel and the supply reel, the brake producing an axially directed frictional braking force against both the supply reel and the take up reel in response to the squeezing the handle sections together.

3. A dental floss holder according to claim 2 wherein the supply reel and the take up reel are rotatably mounted on the shaft.

4. A dental floss holder according to claim 2 wherein the wedge actuated break assembly includes two overlapping endplates, each secured to a different handle section, and a control knob threadably engaging the shaft, the endplates defining at least one wedge that provides the wedge surfaces and produces an axial force between the control knob and the supply reel when the handle sections are squeezed together.

5. A dental floss holder comprising:
   a first elongated support member having a pivot point, a holding section extending from the pivot point on one side thereof to a tip and a handle section extending from the pivot point in a direction opposite the holding section, the handle section terminating with a stationary endplate;
   a second elongated support member having a pivot point, a holding section extending from the pivot point on one side thereof to a tip and a handle section extending from the pivot point in a direction opposite the holding section, the handle section terminating with a removable endplate, the first and second support members being pivotably connected in noncrossing relationship at the respective pivot points with the holding sections and handle sections being in respective opposed, spaced relationship;
   a shaft secured to the second elongated support member and extending along a longitudinal axis between the handle sections of the first and second support members;
   a supply reel mounted on the shaft, the supply reel providing a supply of dental floss;
   a take up reel mounted on the shaft, the holder defining a floss path from the supply reel, between the tips of the first and second support members to the take up reel; and
   a brake assembly disposed to impose an axially directed frictional braking force upon the supply reel and take up reel by coupling a frictional braking force from the removable end plate of the second elongated support member to the supply reel and the take up reel in response to forcing the handle sections of the first and second support members toward each other.

6. A dental floss holder according to claim 5 wherein the brake assembly further comprises:
   a wedge defined by the stationary and removable end plates that causes the axial braking force to be applied to the supply and take up reels as the handle sections of the first and second support members are closed.

7. A dental floss holder according to claim 6 wherein the first endplate is rigidly secured to a rearward end of the first support member and the second endplate is moveably secured to a rearward end of the second support member.

8. A dental floss holder comprising:
   a pair of elongated support members extending in generally parallel spaced relationship on opposite sides of a longitudinally extending central axis, each support member having a holding section extending from a central region to a tip and having a handle section extending from the central region in a direction opposite the holding section, the support members being pivotably connected together in a noncrossing relationship at the central region thereof such that compression of the handle sections closer together tends to spread the tips farther apart, the support members defining a path for passage of dental floss from a supply region between the handle sections past the tips and then to a take up region between the handle sections;

a supply mechanism disposed in the supply region between the handle sections to receive and support a supply of dental floss;

a take up mechanism in the take up region disposed between the handle sections to receive used dental floss, the take up mechanism being adapted to be selectively manipulated by at least one of a thumb and forefinger of a single hand to control tension of dental floss length and tension between the holding sections; and a wedge action brake mechanism including a wedge surface disposed between the handle sections, the wedge action brake mechanism asserting a braking action against the supply mechanism that opposes supplying additional dental floss to the path in response to compression of the handle sections closer together.

9. A dental floss holder according to claim 8 further comprising a shaft coupled to be supported by one of the pair of elongated support members, the shaft being adapted to receive and support the supply mechanism, the take up mechanism and the wedge action braking mechanism.

10. A dental floss holder according to claim 9 wherein the take up mechanism is a reel disposed to be selectively rotated between a thumb and forefinger of a hand holding the handle sections.

11. A dental floss holder comprising:

a first elongated support member having a centrally located pivot point, a floss holding section extending forward of the pivot point and terminating in a first tip and a handle section extending rearward of the pivot point;

a second elongated support member having a centrally located pivot point, a floss holding section extending forward of the pivot point and terminating in a second tip and a handle section extending rearward of the pivot point, the first and second support members being disposed opposite each other in generally parallel spaced relationship and being pivotally joined together at their respective pivot points;

supply and take up mechanisms disposed between the handle sections of the first and second support members, the dental floss holder providing a floss path that extends from the supply mechanism, between the first and second tips and to the take up mechanism; and a wedge actuated brake assembly secured to the handle sections of the first and second support members, the brake assembly including first and second endplates secured respectively to the first and second support members at the handle section thereof and defining a wedge surface which applies a braking force that resists motion of dental floss between the first and second tips in response to pivotal motion of the first and second support members about the pivot point.

12. A dental floss holder according to claim 11, further comprising a shaft extending in generally parallel, spaced relationship between the handle sections of the first and second support members, the shaft having a threaded rearward end;

a control knob threadedly secured to the rearward end of the shaft;

wherein the supply and take up mechanisms comprise supply and take up reels mounted for rotation about the shaft and wherein the first and second endplates extend between the control knob and the supply and take up reels and operate in response to closure of the handle sections of the first and second support members to produce a wedge induced braking force between the control knob and the supply and take up reels.

13. A dental floss holder comprising:

a first elongated support member having a first, centrally located pivot point, a first floss holding section extending forward of the first pivot point and terminating in a first tip and a first handle section extending rearward of the first pivot point;

a second elongated support member having a centrally located second pivot point, a second floss holding section extending forward of the second pivot point and terminating in a second tip, and a second handle section extending rearward of the second pivot point, the first and second support members being disposed opposite each other in generally parallel spaced relationship and being pivotally joined together at their respective first and second pivot points;

an elongated shaft disposed between the first and second handle sections with a forward end secured to the second support member proximate the first and second pivot points, the shaft having a rearward end opposite the forward end;

a floss take up reel disposed for rotation about the shaft;

a floss supply reel disposed for rotation about the shaft, the floss holder defining a floss path that extends from the supply reel, between the first and second tips and to the take up reel;

a control knob threadedly and adjustably secured to the rearward end of the shaft, rearward of the supply and take up reels;

fist and second end plates having first ends secured respectively to the first and second handle sections and opposite second ends disposed in overlapping relationship between the control knob and the supply and take up reels, the first and second endplates having a wedge shaped surface defined between them adjacent the overlapping second ends such that closure of the first and second handle sections toward one another causes the first and second endplates to generate a braking force between the control knob and the supply and take up reels that resists rotation of the supply and take up reels.

14. A dental floss holder according to claim 13 wherein the take up reel is disposed on the shaft adjacent the first and second pivot points and the supply reel is disposed on the shaft adjacent the first and second end plates.

15. A dental floss holder according to claim 13 wherein the take up reel is disposed forward of the supply reel.

16. A dental floss holder according to claim 13 wherein the supply reel includes a hub and a winding of dental floss on the hub, and wherein any braking force asserted against the supply reel is asserted against both the hub and the winding of dental floss thereon.

17. A dental floss holder according to claim 13 wherein one of the first and second endplates has a nonwedge shaped section adjacent the second end thereof that is disposed between the control knob and the supply and take up reels and asserts a braking force on the supply and take up reels that is adjustable by rotating the control knob and is independent of the closure of the handle sections.

18. A dental floss holder according to claim 13 wherein the supply reel includes a hub and a winding of dental floss on the hub and wherein any braking force asserted against the supply reel is asserted both against the hub and against the winding of floss; and wherein one of the first and second endplates has a nonwedge shaped section adjacent the second end having a bore therethrough that receives and supports the rearward end of the shaft, the one endplate asserting a braking force against the supply and take up reels that is selectively adjustable by rotation of the control knob and is independent of any braking force induced by closure of the first and second handle sections.

19. A dental floss holder according to claim 18 wherein the control knob has a forward facing disk shaped surface having a diameter greater than a width of the nonwedge shaped section of the one endplate and wherein the other endplate has a slotted end that is adapted to both receive the nonwedge shaped section of the one endplate and to bear against the disk shaped forward surface of the control knob such that closure of the first and second handle sections causes the first and second endplates to generate a wedge induced braking force on the supply and take up reels.

* * * * *